(12) United States Patent
Schwaibold et al.

(10) Patent No.: US 10,500,359 B2
(45) Date of Patent: Dec. 10, 2019

(54) METHOD AND DEVICE FOR THERAPY OF PERIODIC RESPIRATION

(71) Applicant: WEINMANN GERAETE FUER MEDIZIN GMBH & CO. KG, Hamburg (DE)

(72) Inventors: Matthias Schwaibold, Karlsruhe (DE); Christof Schroeter, Karlsruhe (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 1115 days.

(21) Appl. No.: 14/669,741

(22) Filed: Mar. 26, 2015

(65) Prior Publication Data
US 2015/0273166 A1    Oct. 1, 2015

(30) Foreign Application Priority Data
Mar. 28, 2014   (DE) .................... 10 2014 004 447

(51) Int. Cl.
| | |
|---|---|
| *A61M 16/00* | (2006.01) |
| *A61M 16/16* | (2006.01) |
| *A61M 16/06* | (2006.01) |
| *A61M 16/20* | (2006.01) |

(52) U.S. Cl.
CPC .... *A61M 16/0069* (2014.02); *A61M 16/0003* (2014.02); *A61M 16/024* (2017.08); *A61M 16/06* (2013.01); *A61M 16/16* (2013.01); *A61M 16/20* (2013.01); *A61M 16/0057* (2013.01); *A61M 2016/003* (2013.01); *A61M 2016/0027* (2013.01); *A61M 2205/3334* (2013.01); *A61M 2205/52* (2013.01); *A61M 2230/04* (2013.01); *A61M 2230/30* (2013.01); *A61M 2230/432* (2013.01); *A61M 2230/435* (2013.01)

(58) Field of Classification Search
CPC .......... A61M 16/0003; A61M 16/0069; A61M 16/022; A61M 16/024; A61M 16/026; A61M 16/16; A61M 2016/0027; A61M 2016/003; A61M 2230/005; A61M 2230/40; A61M 2230/42; A61M 2230/43; A61M 2230/432; A61M 2230/435; A61M 2230/46
See application file for complete search history.

(56) References Cited

U.S. PATENT DOCUMENTS

| | | | |
|---|---|---|---|
| 6,349,724 B1 * | 2/2002 | Burton .............. | A61M 16/0057 128/204.18 |
| 6,439,229 B1 | 8/2002 | Du et al. | |
| 6,532,959 B1 | 3/2003 | Berthon-Jones | |
| 6,755,193 B2 | 6/2004 | Berthon-Jones et al. | |
| 6,951,217 B2 | 10/2005 | Berthon-Jones | |
| 7,077,132 B2 | 7/2006 | Berthon-Jones | |
| 7,967,012 B2 | 6/2011 | Berthon-Jones | |
| 8,528,556 B2 | 9/2013 | Berthon-Jones | |

(Continued)

FOREIGN PATENT DOCUMENTS

EP          1083953 A1    12/1999

*Primary Examiner* — Catharine L Anderson
(74) *Attorney, Agent, or Firm* — Abel Schillinger, LLP (57) ABSTRACT

The invention relates to a method and a device for treating Cheyne-Stokes respiration, periodic respiration and central or mixed apnea. If the respiration waxes and wanes periodically, there is pressure support in phases of periodic respiration, taking into account the natural patient respiration.

15 Claims, 4 Drawing Sheets

(56) References Cited

U.S. PATENT DOCUMENTS

| | | |
|---|---|---|
| 8,857,430 B2 | 10/2014 | Berthon-Jones |
| 2003/0154979 A1 | 8/2003 | Berthon-Jones |
| 2003/0192544 A1 | 10/2003 | Berthon-Jones et al. |
| 2004/0237963 A1 | 12/2004 | Berthon-Jones |
| 2005/0211248 A1 | 9/2005 | Lauk et al. |
| 2006/0243281 A1 | 11/2006 | Berthon-Jones |
| 2011/0265794 A1 | 11/2011 | Berthon-Jones |
| 2011/0284003 A1 | 11/2011 | Douglas et al. |
| 2014/0069430 A1 | 3/2014 | Berthon-Jones |
| 2015/0013679 A1 | 1/2015 | Berthon-Jones |
| 2015/0128942 A1* | 5/2015 | Tatkov ................ A61M 16/024 128/203.14 |

* cited by examiner

METHOD AND DEVICE FOR THERAPY OF PERIODIC RESPIRATION

CROSS-REFERENCE TO RELATED APPLICATIONS

The present application claims priority under 35 U.S.C. § 119 of German Patent Application No. 10 2014 004 447.5, filed Mar. 28, 2014, the entire disclosure of which is expressly incorporated by reference herein.

BACKGROUND OF THE INVENTION

1. Field of the Invention

The invention relates to a method and a device for treating Cheyne-Stokes respiration, periodic respiration and central or mixed apnea.

2. Discussion of Background Information

In some patients, their own respiratory drive is so disturbed that the respiration waxes and wanes periodically. Conventional methods for support increase the ventilation pressure in phases of periodic respiration.

EP 1083953, the disclosure of which is incorporated herein in its entirety, describes a method for therapy of Cheyne-Stokes respiration. Here, there is a continuous measurement and establishment of the volume of the ventilation during the last few minutes, wherein said volume is averaged. Moreover, a target volume—typically 90%—is predetermined, which emerges from the relatively long-term ventilation of the preceding ventilation. If there is a difference between the target volume and the current volume, the pressure support by the ventilator is increased. As a result, the current respiration of the patient should be supported by a pressure lift in such a way that the target volume is reached.

A disadvantage of this method is that the approach does not take into account the fact that the respiratory state can change and that respiration overall tends to be chaotic. Here, a change in the respiratory state brings about a modified target ventilation.

By way of example, if the target volume is established over a period of time during which the patient breathed intensely—for example in an awake state—and if this target volume is compared to the currently little pronounced respiration of the patient while sleeping, the algorithm from EP 1083953 would lift the pressure support above the measure of the natural respiration of the patient while sleeping because, of course, the previously established target volume is based on the intense respiration in the awake state.

It is therefore advantageous to be able to specify an adaptive pressure support so as to compensate for variations in the respiratory drive of the patient, said pressure support, however, taking the current natural respiration of the patient into account.

SUMMARY OF THE INVENTION

The present invention provides a ventilator which comprises a controllable respiratory gas source for predetermining ventilation parameters in the respiratory gas supply of a patient with periodic respiration, one or more elements for establishing a current measure of a ventilation parameter, one or more storage elements for storing a measure of a preceding ventilation parameter in a recallable manner, one or more comparison elements for deriving a measure for the change (increase/decrease) in the current ventilation parameter compared to the preceding ventilation parameter, one or more elements for establishing a current measure of the respiration, one or more storage elements for storing a measure of the preceding respiration in a recallable manner, one or more comparison elements for deriving a measure for the change (increase/decrease) in the current respiration compared to the preceding respiration, one or more comparison elements for deriving a measure for the change (increase/decrease) in the respiratory exertion from at least one of the measures, a control apparatus which controls at least one ventilation parameter dependent on the measure.

BRIEF DESCRIPTION OF THE DRAWINGS

In the accompanying drawings.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
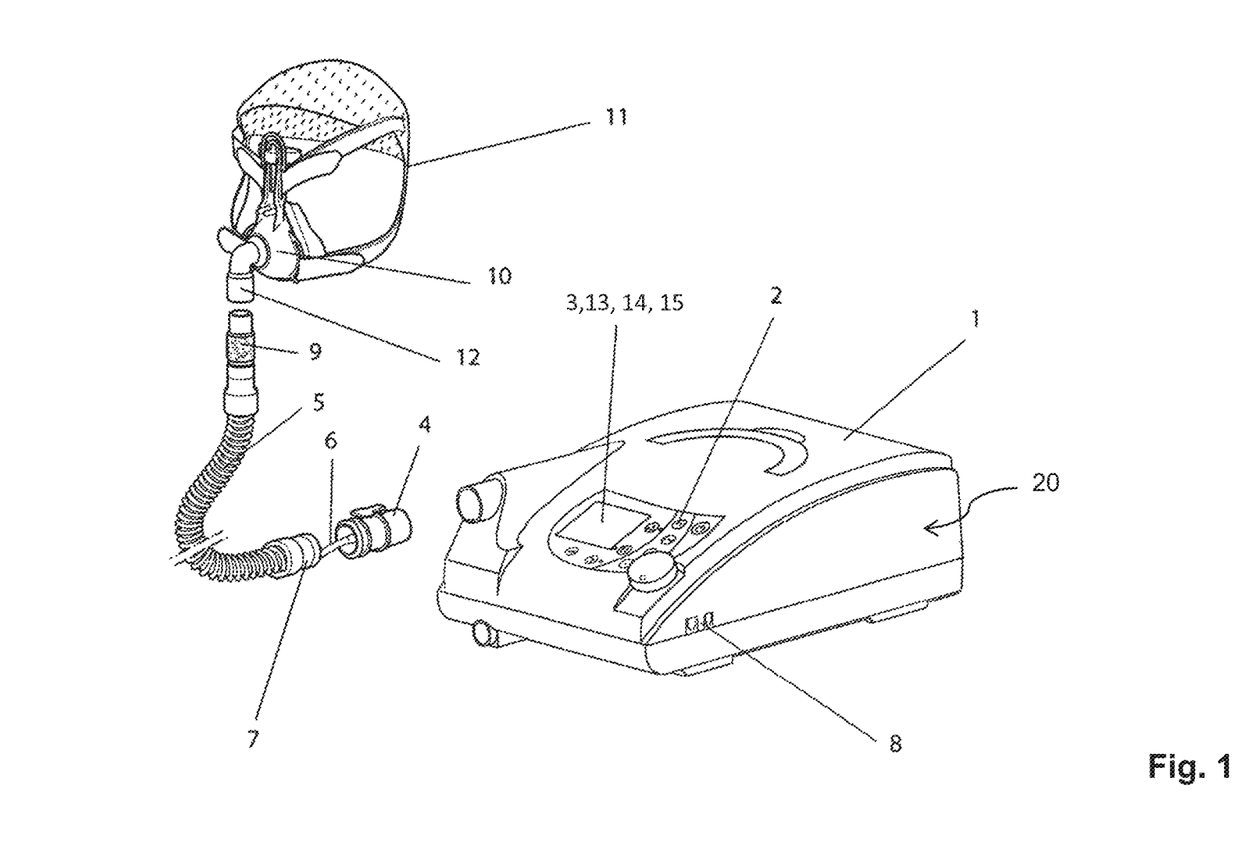
FIG. 1 shows the basic setup of a device for ventilation.

FIG. 1 shows the basic setup of a device for ventilation. In the region of an instrument housing (1) of the ventilator (20), which has a respiratory gas source in the instrument interior, there are arranged an operating element (2) and an operation and information system (3) consisting of a display (13), a touch-sensitive input unit (15) with at least one control panel (14). A control unit (19) serves to control the real-time operation of the ventilator. A connecting tube (5) is connected by way of a coupling (4). An additional pressure measuring tube (6) can extend along the connecting tube (5), said pressure measuring tube being connectable to the instrument housing (1) by way of a pressure input nozzle (7). In order to enable data transfer, the instrument housing (1) has at least one interface (8). Moreover, a humidifier (30) can be adapted. An expiratory element (9) is arranged in the region of an extent of the connecting tube (5) distant from the instrument housing (1). An expiratory valve can likewise be used.

FIG. 1 moreover shows a patient interface, which is embodied as a ventilation mask (10) and implemented as nasal mask. Attachment in the region of the head of a patient can be brought about by way of headgear (11). In the region of the extent thereof facing the connecting tube (5), the patient interface (10) has a coupling element (12). Data, such as e.g. dead space volume, can be input and/or output by way of the interface (8). The interfaces can be implemented in a manner connected by wires, as an infrared interface, as a Bluetooth interface or as a USB. Preferably, provision is also made for a card slot. The interface (8) can also be embodied as a LAN interface or any other interface for connection to the Internet. In the region of an instrument housing, an oxygen connection valve can be adapted to the device for ventilation. It is conceivable to additionally enrich the respiratory gas with oxygen so as to improve the patient care. By way of the interface (8)—for example embodied as a card slot or USB—it is also possible for data external to the therapy to be loaded into the ventilator according to the invention or to be executed thereby. By way of example, it is considered to display photos or videos in the region of the display via the interface (8) by using storage media. The user must confirm a query in the operating field—if the instrument identifies external storage media—whereupon the data are selectively stored in the region of the ventilator or executed. The ventilator (20) according to the invention is designed in such a way that it can be connected to a patient by way of a tube and a patient interface so as to provide ventilation. It comprises a source for respiratory gas, which, for example, is embodied as an electric motor with an impeller, and at least one sensor apparatus (21) for establishing pressure and/or flow and/or volume of the respiratory gas, and also a control unit (19), which is configured in such a way that it determines, for each respiratory cycle, a respiratory gas pressure on the basis of a predetermined value for the patient and/or on the basis of measurement signals for the pressure and/or flow and/or volume parameters, and regulates the source for respiratory gas in such a way that the respiratory gas pressure is generated.

The control unit (19) is furthermore configured in such a way that it determines the current pressure and/or flow and/or the volume of respiratory gas and displays the current value by way of the operation and information system (3) connected to the control unit. The control unit (19) is moreover configured in such a way that it, by way of a statistics module (23), determines changes in the trend in relation to one or more parameters over a period of time, wherein the changes in the trend can be stored in the memory (22) or can be displayed on the display.

Furthermore, the control unit (19) compares those parameter values which have been predetermined by a user, e.g. upper and lower pressure limits or a maximum tolerable number of apnea per unit time, or a maximum tolerable leakage, with the current values and generates user information in relation to deviations from the specification. The user information is preferably visualized graphically in the region of the display (14) by way of the operation and information system (3).

Thus, for example, apnea and hypopnea are identified from the measured respiratory flow by way of a reduction in the respiratory (time) volume for a time duration of at least 3 seconds. Additionally, snoring is identified by way of pressure and flow variations, and flattening is identified by way of the inspiratory flow contour. From this, the statistics module (23) calculates indices for each sufficiently long night-time therapy, specifically: AHI (=number of apnea+hypopnea per artifact-free therapy duration), RDI (=number of all respiratory events per artifact-free therapy duration), proportion of breaths with flattening, proportion of breaths with snoring. Preferably, data which allow deductions to be made about the usage behavior or the usage duration of the instrument by the patient are also established. These data are established and stored on a daily, weekly or monthly basis by the statistics module. Where necessary, these usage data are stored, possibly together with an instrument identification, instrument-related data and/or patient data or patient identification.

By way of example, instrument-related data can be instrument type, serial number, firmware version, electronics version, hours of operation of one or more components and a fault memory. By way of example, patient-related data can contain name, identity number, date of birth, insurance number, prescription number or location.

Patient entries such as e.g. subjective feeling, therapy side effects, degree of severity of the disease or medication can likewise be stored and depicted.

Moreover, it is also possible to store and display instrument settings such as pressure (limits), frequency, Ti/T, target volume, trigger stage, comfort settings, values in relation to air temperature and air humidity and humidifier level, just like usage data such as e.g. number of hours on individual days or within specific periods of time, mean number of hours, minimum/maximum number of hours, proportion of days where the use exceeds a threshold, usage information in relation to the humidifier, etc.

In addition to the above-described indices such as AHI and RHI, it is possible to establish, store and display more therapy quality indices, such as snoring index, RERA index, oAHI, zAHI, index for periodic respiration/CS-respiration, volume index, sleep quality index, oxygen index, $CO_2$ index, respiratory exertion index, trigger quality index, proportion of breaths with/without spontaneous respiration or at specific pressure limits, percentiles of pressure, frequency, volume, degree of obstruction, Ti/T or similar parameters, blood pressure index, blood sugar index, cardiac frequency index, by means of the statistic module.

The operation and information system (3) for a ventilator (20) comprises an illuminated or back-illuminated display (13) for displaying control panels (14) or information for the user and an e.g. touch-sensitive input unit (15), which can also be embodied as a mechanical input unit, in the spatial vicinity of the depicted control panel (14). In a specific embodiment, this is e.g. a human-machine interface in the form of a so-called touchscreen, a person skilled in the art being aware of different types, which all come into question as a component of the operation and information system (3) according to the invention. At least a first control panel and a second control panel are depicted in the region of the display. The control unit (19) is embodied to depict the menu on the display (13). A processing unit (18), which is coupled to the display (13) and the touch-sensitive input unit (15), is configured to register an operation of the control panel (14) by way of the input unit (15) and, dependent thereon, actuate a function of the menu by way of the control unit (19).

The memory (22) can be used to store current settings, the system status, patient data and ventilation control software, which is carried out by the control unit. The control unit can moreover be connected to a storage device, such as e.g. a storage medium buffered by a battery, a memory card, a hard disk drive, a disk drive, a magnetic tape drive or any other storage medium for storing patient data and associated ventilator operation parameters. The control unit accepts entries that are received by the operating system in order to control the ventilator (20). The ventilator can moreover have status indicators, a display in order to store patient data and ventilator settings, and an audio generator in order to provide audible specifications in relation to the status of the ventilator.

Figure 2:
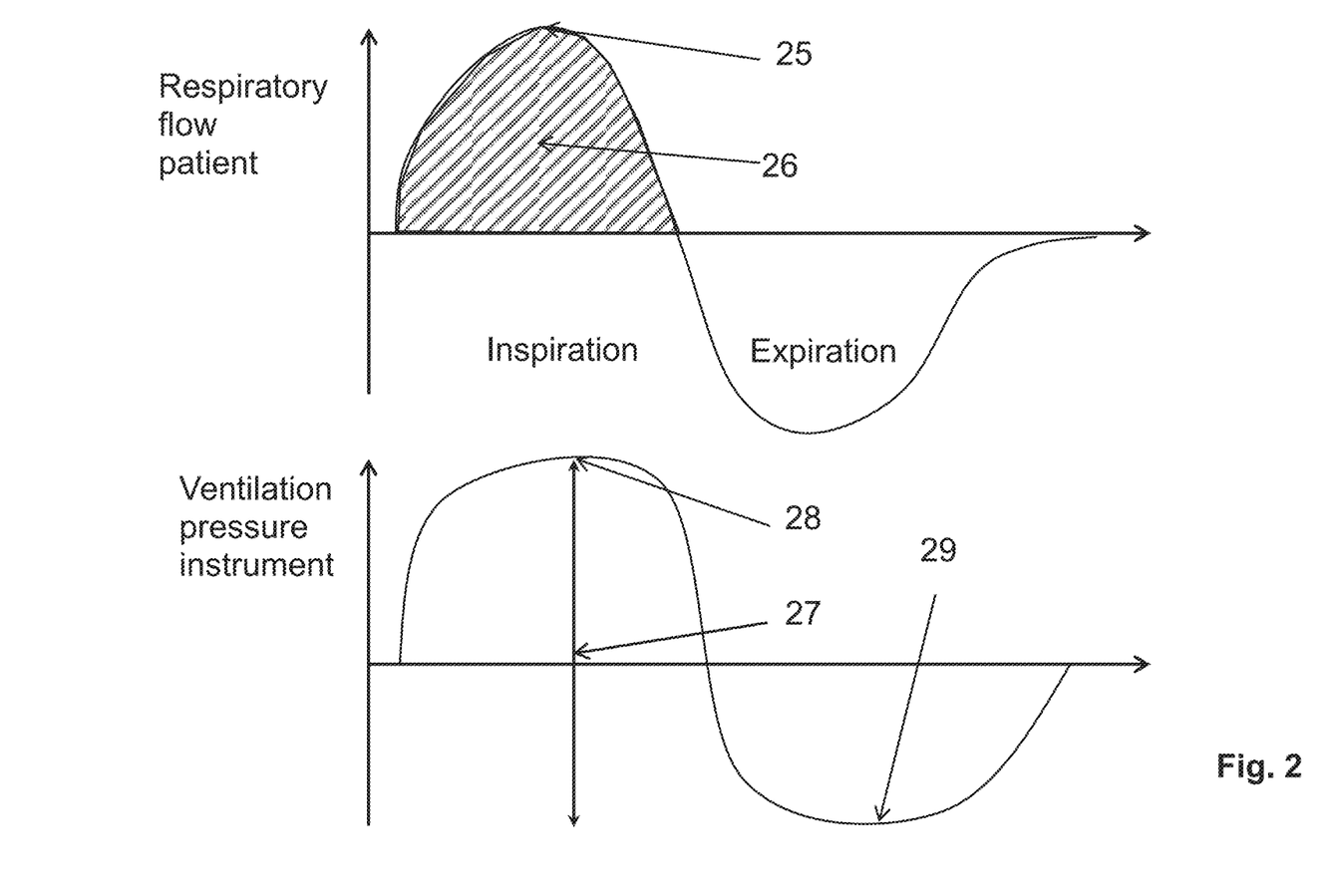
FIG. 2 shows, at the top, the profile of the respiration of the patient and at the bottom, shows the profile of the pressure support by the ventilator.

FIG. 2 shows, at the top, the profile of the respiration of the patient. Here, the flow was established and recorded with the aid of a flow sensor. The peak flow (25), approximately in the middle of the inspiration, and the tidal volume (26), which the patient breaths in during the inspiration, are plotted. The minute volume is the inspiratory volume per minute and, in accordance with FIG. 2, can be calculated at any time.

At the bottom, FIG. 2 shows the profile of the pressure support (27) by the ventilator. Here, the pressure was established and recorded by means of a pressure sensor. The IPAP (28), which is reached in approximately the middle of the inspiration, is plotted. Moreover, the expiratory pressure EPAP (29) is plotted. The difference between IPAP and EPAP is the pressure support (27). The ventilation with pressure support (PDIFF) increases the tidal volume and/or minute volume of the patient respiration as a result of respiratory phase synchronous application of the pressures and therefore improves the ventilation of the lung.

Figure 3:
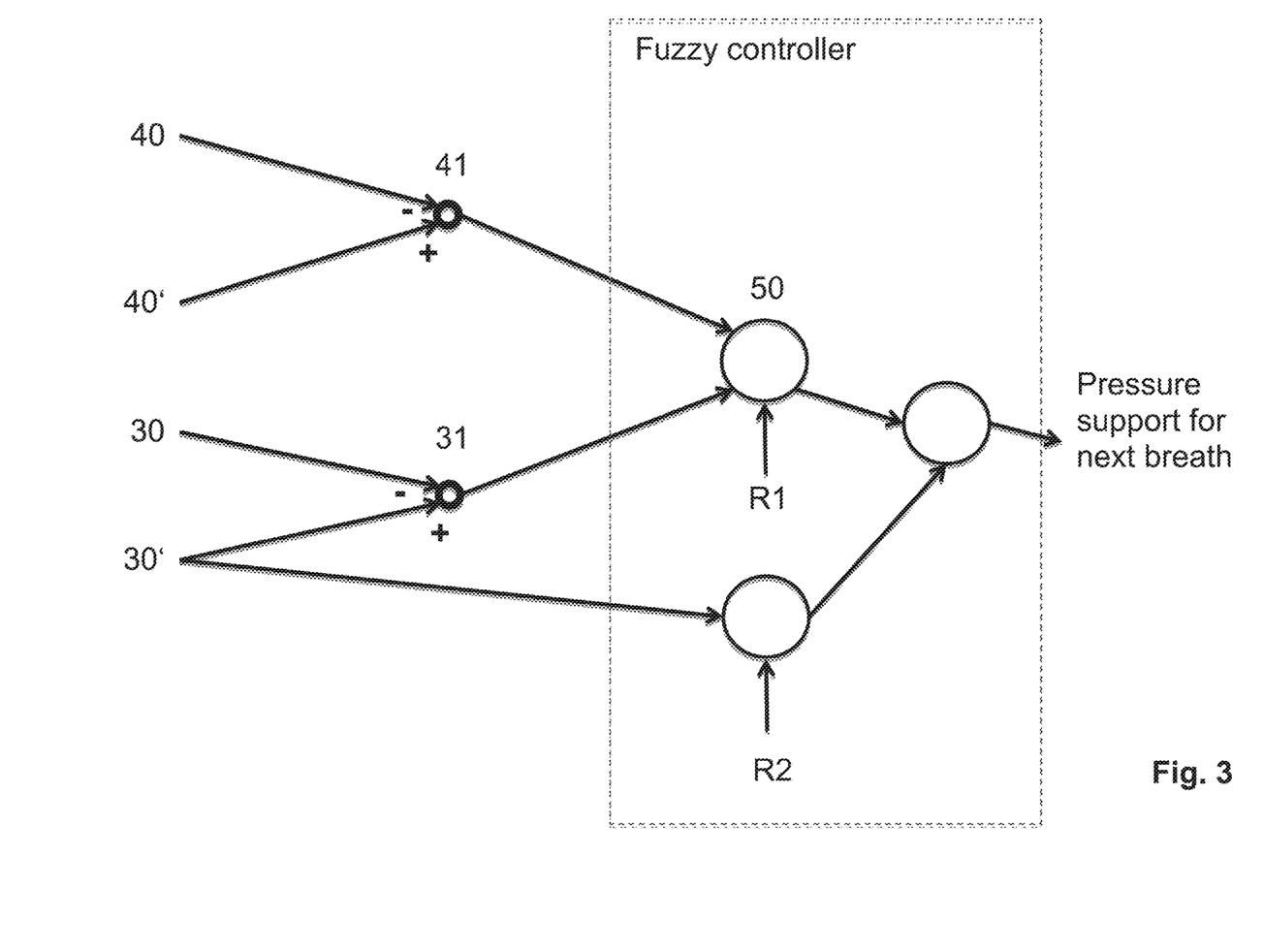
FIG. 3 schematically shows aspects of an exemplary embodiment of the ventilator of the present invention.

FIG. 3 schematically illustrates the operation of a ventilator according to the present invention which comprises a controllable respiratory gas source for predetermining ventilation parameters in the respiratory gas supply of a patient with periodic respiration, means for establishing a current measure of a ventilation parameter (30'), storage means for storing a measure of a preceding ventilation parameter (30) in a recallable manner, comparison means for deriving a measure for the change (31) (increase/decrease) in the current ventilation parameter compared to the preceding ventilation parameter, means for establishing a current measure of the respiration (40'), storage means for storing a measure of the preceding respiration (40) in a recallable manner, comparison means for deriving a measure (41) for the change (increase/decrease) in the current respiration compared to the preceding respiration, comparison means for deriving a measure for the change (increase/decrease) in the respiratory exertion (50) from at least one of the measures (31, 41), and a control apparatus which controls at least one ventilation parameter dependent on the measure (50).

The ventilator establishes a measure for the current respiration by virtue of the respiration of the patient being recorded by means of a flow and/or pressure sensor. The measure for the current respiration (40') is established from the pressure and/or flow profile, for example as peak flow (25) and/or volume and/or time volume and/or current flow and/or tidal volume (26) and/or relative volume and/or minute volume. Here, the measure for the current respiration (40') preferably only relates to one breath, namely the last one. The ventilator stores this measure of the current respiration in a storage medium. Since the ventilator records a measure of the current respiration (40') continuously during operation, specifically with each breath, the storage medium has, chronologically, the values of the last and second-to-last breaths. By calculation, the ventilator establishes a measure for the change (41) (increase/decrease) in the respiration from the values of the measures of the respiration of the last (40') and second-to-last breaths (40).

The ventilator establishes a measure for the current ventilation (e.g. pressure support, pressure lift or frequency) by virtue of the ventilation by the instrument being recorded by means of a flow and/or pressure sensor or by virtue of the applied values being used. The measure for the current ventilation (30') is for example established from the pressure and/or flow profile as peak flow and/or volume and/or time volume and/or current flow and/or tidal volume and/or relative volume and/or minute volume. Here, the measure for the current ventilation (30') preferably only relates to one breath, namely the last one.

The ventilator stores this measure of the current ventilation in a storage medium. Since the ventilator records a measure of the current ventilation (30') continuously during operation, specifically with each breath, the storage medium has, chronologically, the values of the last and second-to-last breaths.

By calculation, the ventilator establishes a measure for the change (31) (increase/decrease) in the ventilation (pressure support) from the values of the measures of the respiration of the last (30') and second-to-last (30) breaths.

By calculation, the ventilator establishes a measure for the change (increase/decrease) in the respiratory exertion (50) of the patient from the values of the measures of the change (increase/decrease) in the ventilation (31) and change (increase/decrease) in the respiration (41). By way of example, the ventilator thus establishes the respiratory exertion (50) for the second-to-last breath and for the last breath and compares said breaths. The respiratory exertion (50) of the patient serves as a first reference value (R1). By way of example, an unchanging respiratory exertion (50) of the patient serves as a first reference value (R1).

The ventilation (31, for example as unchanging pressure support) of the patient serves as a second reference value (R2). By way of example, an unchanging ventilation (31) of the patient serves as a second reference value (R2). If there is no change in the respiratory exertion and no change in the ventilation, the pressure support for the next breath remains unchanged. The ventilator can take both reference values (R1 and R2) into account for the closed-loop control of the pressure support for the next breath. Alternatively, the ventilator can also only take R1 into account.

The ventilator reacts to a change in the value of the respiratory exertion (50) of the patient with a change in the ventilation, i.e., for example, in the pressure support. The pressure support is typically modified, preferably in a manner proportional to the change in the respiratory exertion. If the respiratory exertion (50) of the patient sinks, the ventilator reacts with an increase in the pressure support. By way of example, IPAP and EPAP are modified in such a way that the pressure lift is increased. Alternatively, it is also possible only to lift the IPAP. Likewise, it is also possible only to lower the EPAP. The pressure support is typically modified, preferably in a manner proportional to the change in the respiratory exertion.

By way of example, the ventilation (e.g. pressure lift or frequency) is controlled anti-cyclically in relation to the value of the respiratory exertion of the patient, for example with an increase of the ventilation pressure in the region of 0.5-4 hPa when the respiration drops by 20%.

The anti-cyclical ventilation is amplified or weakened depending on a preceding hyperventilation. The greater the hyperventilation is, the greater the amplification.

Successive breaths with increased volume count as a measure for the hyperventilation. The search window is e.g. the duration of a CS respiratory cycle (i.e. the last approximately 90 seconds); thereafter, the level of the amplification is largely decayed.

The resulting change in the ventilation still is limited prior to application to the patient, e.g. to at most 4 hPa difference in the pressure lift between 2 breaths.

The ventilation can occur between 2 breaths on the basis of the evaluation of the last breath, or directly within the current breath by evaluating the current respiration profile.

If the quotient of current volume to normal volume (rRMV) (this is updated every 2 minutes) decreases, PDIFF is increased and vice versa. Here, the magnitude of the PDIFF change depends not only on the magnitude of the rRMV change, but additionally on the preceding hyperventilation level: the higher the latter is, the more dynamic the reaction is.

In CS patients, the hyperventilation can be seen to be the trigger of the respiration instability. Therefore, in the case of hyperventilation, the rRMV of the patient falling under its "target volume" (that would be approximately 100% rRMV) is not awaited, but rather the starting hyperventilation is picked up by increasing PDIFF when the rRMV begins to fall.

The strength of the hyperventilation peak can be considered to be a measure for the characteristic of the CS respiration. Therefore, this value is used as amplification factor. Therefore, a reaction to the periodicity with adaptive PDIFF dynamics is achieved. By way of example, this also leads to the patient not being re-awoken by a PDIFF increase during the falling asleep stage, when the volume slightly reduces in a continuous and completely physiological manner, because the volume reduction is not preceded by hyperventilation.

Control limits can be set for (E)EPAP, pressure lift and frequency. For the pressure lift, a value for the basal support of the respiratory muscles (pressure lift during normal respiration) is preferably additionally selectable.

During phases with largely stable respiration (small changes), the controller changes the pressure lift in a step-by-step manner to the preselected basal support. Phases with largely stable respiration (small changes) are distinguished by virtue of the respiratory exertion from breath to breath deviating by less than 20%, preferably by less than 10%, particularly preferably by less than 5%. Phases with largely stable respiration (small changes) are alternatively also distinguished by virtue of the pressure support from breath to breath deviating by less than 20%, preferably by less than 10%, particularly preferably by less than 5%.

Figure 4:
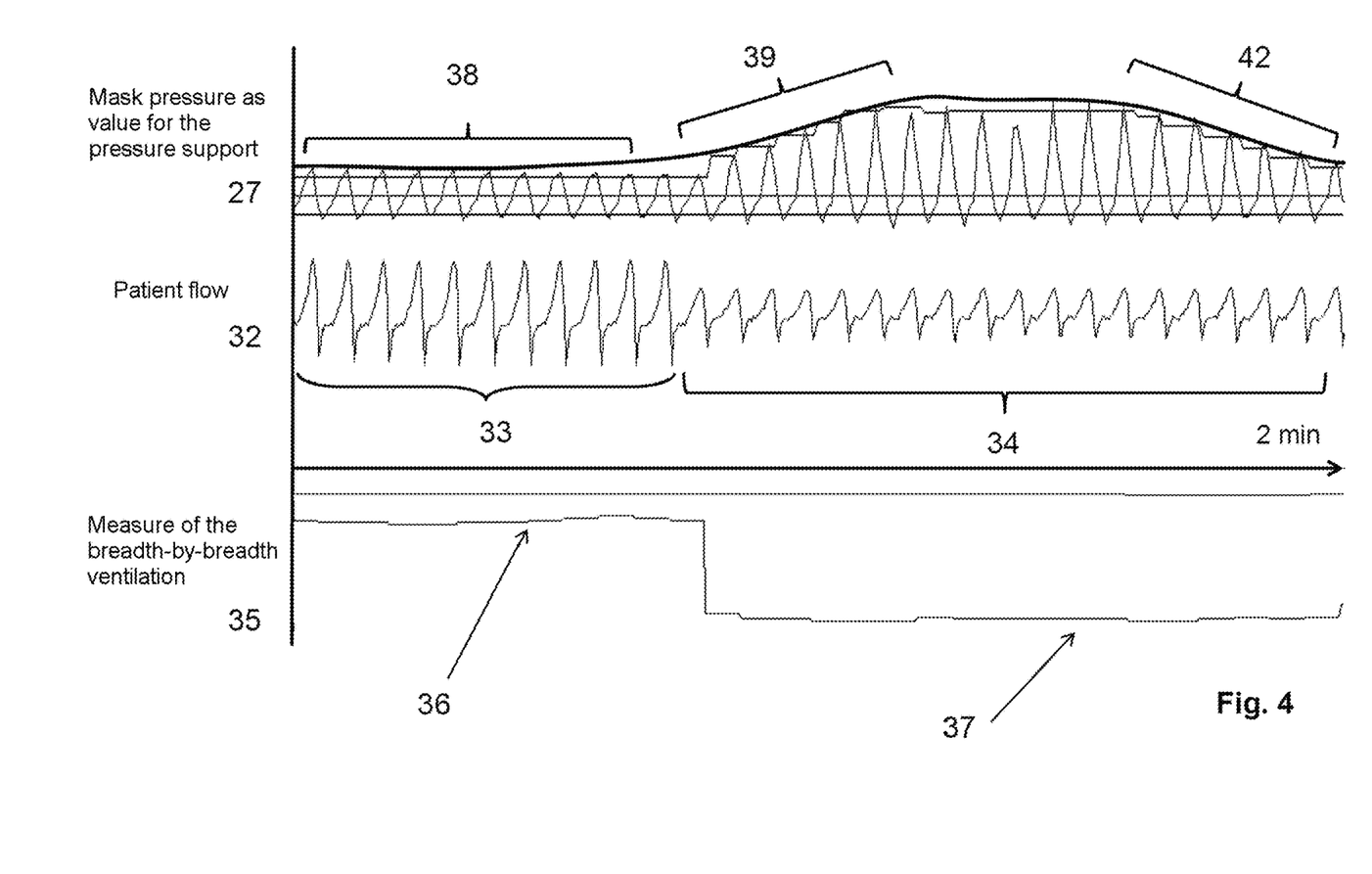
FIG. 4 schematically shows how the ventilator establishes a measure for the current respiration by virtue of the respiration of the patient being recorded by means of a flow sensor ("patient flow") and additionally establishes a measure of the "breath-by-breath ventilation" for the current respiration from the pressure and/or flow profile and/or volume and/or time volume and/or tidal volume and/or minute volume.

FIG. 4 shows: the ventilator establishes a measure for the current respiration by virtue of the respiration of the patient being recorded by means of a flow sensor ("patient flow", 32).

The ventilator additionally establishes a measure of the "breath-by-breath ventilation" (35) for the current respiration from the pressure and/or flow profile and/or volume and/or time volume and/or tidal volume and/or minute volume.

The ventilator stores this measure of "breath-by-breath ventilation" (35) in a storage medium (22). By way of example, the "breath-by-breath ventilation" (35) is considered to be an index value up to 100% and stored, wherein 100% (36) means that the value was stable for a long period of time.

From the comparison between the central curve "patient flow" (32) with the lower curve "breath-by-breath ventilation" (35), it is possible to identify that the breath-by-breath ventilation (37) also reduces when the patient flow reduces (34), from 100 to 50% in this example. In accordance with the method explained in the description relating to FIG. 3, the ventilator reacts with an unchanging pressure support (38) in the case of unchanging ventilation (36). If the ventilation reduces (37), for example because the patient flow reduces, the ventilator increases the pressure support (39) by virtue of the IPAP and/or the EPAP being adapted until a long-term (over at least 2 breaths) stable ventilation is established. Once the ventilation is stable again, the ventilator reduces the pressure support (42) by virtue of the IPAP and/or the EPAP being adapted.

While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

To sum up, the present invention provides:

1. A ventilator which comprises
a controllable respiratory gas source for predetermining ventilation parameters in the respiratory gas supply of a patient with periodic respiration,
one or more elements (21, 22) for establishing a current measure of a ventilation parameter (30),
one or more storage elements (22) for storing a measure of a preceding ventilation parameter (30) in a recallable manner,
one or more comparison elements for deriving a measure for the change (31) (increase/decrease) in the current ventilation parameter (30') compared to the preceding ventilation parameter (30),
one or more elements (21) for establishing a current measure of the respiration (40'),
one or more storage elements (22) for storing a measure of the preceding respiration (40) in a recallable manner,
one or more comparison elements for deriving a measure (41) for the change (increase/decrease) in the current respiration compared to the preceding respiration,
one or more comparison elements for deriving a measure for the change (increase/decrease) in the respiratory exertion (50) from at least one of the measures (31, 41), and
a control apparatus which controls at least one ventilation parameter dependent on the measure (50).

2. The ventilator according to item 1, wherein the control apparatus controls at least one ventilation parameter dependent on the measure (50) with the object of achieving a gradient of 0 for the measure (50).

3. The ventilator according to items 1 or 2, wherein the control apparatus controls the at least one ventilation parameter dependent on the measure (50) with the object of achieving a gradient of 0 for the measure (30).

4. The ventilator according to at least one of the preceding items, wherein the control apparatus controls at least the IPAP pressure and/or the EPAP pressure for the subsequent breath dependent on the change in the respiratory exertion (50) in the preceding breaths.

5. The ventilator according to at least one of the preceding items, wherein the control apparatus leads the pressure lift, i.e. the difference between the IPAP pressure and EPAP pressure, to a preselected basal support in a step-by-step manner in phases with largely stable respiration, in which the respiratory exertion deviates by less than 20% from breath to breath.

6. The ventilator according to at least one of the preceding items, wherein the pressure support is adapted on a breath-by-breath basis in the case of changes in the ventilation during the night.

7. The ventilator according to at least one of the preceding items, wherein recordings of the pressure curve and/or flow curve and/or respiratory frequency of the natural respiration of the patient are used, at least from time to time, for modulating the pressure support.

8. The ventilator according to at least one of the preceding items, wherein the recording of the pressure curve and/or flow curve and/or respiratory frequency of the natural respiration of the patient is used, at least from time to time, for calculating a safety frequency for the ventilation.

9. The ventilator according to at least one of the preceding items, wherein the expiratory positive airway pressure (EPAP) can be set from 2 to 15 cm H2O.

10. The ventilator according to at least one of the preceding items, wherein different pressure profiles can be applied for inspiration and expiration.

11. The ventilator according to at least one of the preceding items, wherein obstructions are identified by FOT and/or flattening and/or snoring and/or apnea and/or a flow response to mandatory ventilation.

12. The ventilator according to at least one of the preceding items, wherein the cardiac output or blood pressure or cardiac frequency or SpO2 or CO2 are established by means of an adaptable module and the measured variables of cardiac output or blood pressure or cardiac frequency or SpO2 or CO2 are used for calculating the pressure support.

13. The ventilator according to at least one of the preceding items, wherein the closed-loop control of the power of a humidifier connected to the ventilator is carried out dependent on the measure of the pressure support.

14. The ventilator according to at least one of the preceding items, wherein a pressure support that is lower than the ideal calculated one is applied during an initial accustoming phase.

15. A method for controlling the respiratory gas supply of a patient with periodic respiration, wherein the method comprises:

establishing a current measure of a ventilation parameter (30), storing, in a recallable fashion, a preceding ventilation parameter (30), establishing the change (31) (increase/decrease) in the current ventilation parameter compared to the preceding ventilation parameter, establishing a current measure of the respiration (40), storing, in a recallable fashion, a measure of the preceding respiration (40), establishing a measure (41) for the change (increase/decrease) in the current respiration compared to the preceding respiration, establishing a measure for the change (increase/decrease) in the respiratory exertion (50) from at least one of the measures (31, 41), controlling at least one ventilation parameter dependent on the measure (50).

What is claimed is:

1. A ventilator, wherein the ventilator comprises
a controllable respiratory gas source for predetermining ventilation parameters in a respiratory gas supply of a patient with periodic respiration,
one or more elements for establishing a measure of a current ventilation parameter of the controllable respiratory gas source,
one or more first storage elements for storing a measure of a preceding ventilation parameter of the controllable respiratory gas source in a recallable manner,
one or more first comparison elements for deriving a first measure of a change (increase/decrease) in a current ventilation parameter of the controllable respiratory gas source compared to a preceding ventilation parameter of the controllable respiratory gas source,
one or more elements for establishing a measure of a current respiration, one or more second storage elements for storing a measure of a preceding respiration in a recallable manner,
one or more second comparison elements for deriving a second measure of a change (increase/decrease) in a current respiration compared to a preceding respiration,
one or more third comparison elements for deriving a third measure of a change (increase/decrease) in a respiratory exertion from at least one of the first and second measures, and
a control apparatus which controls at least one ventilation parameter dependent on the third measure.

2. The ventilator of claim 1, wherein the control apparatus is configured to be capable of controlling the at least one ventilation parameter dependent on the third measure to achieve a gradient of 0 for the third measure.

3. The ventilator of claim 1, wherein the control apparatus is configured to be capable of controlling the at least one ventilation parameter dependent on the third measure to achieve a gradient of 0 for the measure of a preceding ventilation parameter.

4. The ventilator of claim 1, wherein the control apparatus controls at least an IPAP pressure and/or an EPAP pressure for a subsequent breath dependent on a change in respiratory exertion (third measure) in preceding breaths.

5. The ventilator of claim 4, wherein the control apparatus leads a pressure lift, i.e. a difference between IPAP pressure and EPAP pressure, to a preselected basal support in a step-by-step manner in phases with largely stable respiration in which respiratory exertion deviates by less than 20% from breath to breath.

6. The ventilator of claim 1, wherein pressure support is adapted on a breath-by-breath basis in case of changes in ventilation during nighttime.

7. The ventilator of claim 1, wherein recordings of at least one of a pressure curve, a flow curve, or a respiratory frequency of a natural respiration of a patient are used, at least from time to time, for modulating a pressure support.

8. The ventilator of claim 1, wherein a recording of at least one of a pressure curve, a flow curve, or a respiratory frequency of a natural respiration of a patient is used, at least from time to time, for calculating a safety frequency for the ventilation.

9. The ventilator of claim 1, wherein an expiratory positive airway pressure (EPAP) can be set from 2 to 15 cm H2O.

10. The ventilator of claim 1, wherein different pressure profiles can be applied for inspiration and expiration.

11. The ventilator of claim 1, wherein obstructions are identified by at least one of frequency-only tracking (FOT), flattening, snoring, apnea or a flow response to mandatory ventilation.

12. The ventilator of claim 1, wherein at least one of cardiac output, blood pressure, cardiac frequency, SpO2 or CO2 is established by means of an adaptable module and measured variables of the at least one of cardiac output, blood pressure, cardiac frequency, SpO2 or CO2 are used for calculating pressure support.

13. The ventilator of claim 1, wherein control of a power of a humidifier connected to the ventilator is carried out dependent on a measure of pressure support.

14. The ventilator of claim 1, wherein during an initial accustoming phase a pressure support that is lower than an ideal calculated one is applied.

15. A method for controlling the respiratory gas supply of a patient with periodic respiration using the apparatus of claim 1, wherein the method comprises:
- establishing a measure of a current ventilation parameter,
- storing, in a recallable fashion, a measure of a preceding ventilation parameter,
- establishing a first measure of a change (increase/decrease) in a current ventilation parameter compared to a preceding ventilation parameter,
- establishing a measure of a current respiration,
- storing, in a recallable fashion, a measure of a preceding respiration,
- establishing a second measure for a change (increase/decrease) in a current respiration compared to a preceding respiration,
- establishing a third measure for a change (increase/decrease) in a respiratory exertion from at least one of the first and second measures,
- controlling at least one ventilation parameter dependent on the third measure.

* * * * *